United States Patent [19]  [11]  4,440,662
Tsuzuki et al.  [45]  Apr. 3, 1984

[54] CLEANING COMPOSITION FOR CONTACT LENSES

[75] Inventors: Akira Tsuzuki; Takeo Kibe, both of Nagoya; Shunichi Hioki, Ichinomiya, all of Japan

[73] Assignee: Toyo Contact Lens Co., Ltd., Nagoya, Japan

[21] Appl. No.: 417,477

[22] Filed: Sep. 13, 1982

[30] Foreign Application Priority Data

Oct. 22, 1981 [JP] Japan .................................. 56-167897

[51] Int. Cl.³ .......................... C11D 1/44; C11D 1/825
[52] U.S. Cl. ................................ 252/106; 252/174.22; 252/174.23; 252/529; 252/548; 252/DIG. 14
[58] Field of Search ........... 252/106, 544, 548, 174.22, 252/174.23, DIG. 1, 529

[56] References Cited

U.S. PATENT DOCUMENTS

| | | | |
|---|---|---|---|
| 3,650,965 | 3/1972 | Cantor et al. | 252/106 |
| 3,882,036 | 5/1975 | Krezanoski et al. | 252/106 |
| 3,954,644 | 5/1976 | Krezanoski et al. | |
| 4,013,576 | 3/1977 | Loshaek | 252/106 |
| 4,323,467 | 4/1982 | Fu | 252/106 |
| 4,356,100 | 10/1982 | Sherman | 252/106 |

FOREIGN PATENT DOCUMENTS 48-32784  5/1973  Japan .

*Primary Examiner*—P. E. Willis, Jr.
*Attorney, Agent, or Firm*—Oblon, Fisher, Spivak, McClelland & Maier

[57] ABSTRACT

A cleaning composition for contact lenses, comprises, as the major component, polypropyleneoxide-polyethyleneoxide block copolymers (Pluronic type) and/or condensation products of polypropyleneoxide-polyethyleneoxide block copolymers with ethylene diamine (Tetronic type), in which said major component is a mixture of those having an ethyleneoxide content of from 35 to 55% by weight and a molecular weight of from 1,500 to 10,000 and those having an ethyleneoxide content of from 70 to 90% by weight and a molecular weight of at least 4,000.

13 Claims, No Drawings

CLEANING COMPOSITION FOR CONTACT LENSES

BACKGROUND OF THE INVENTION

1. Field of the Invention

The present invention relates to a cleaning composition for contact lenses. More particularly, it relates to a cleaning composition particularly useful for water-absorptive contact lenses.

2. Description of the Prior Art

Heretofore, various kinds of contact lenses have been used. As typical contact lenses, there are water-nonabsorptive contact lenses made of polymethyl methacrylate or silicone rubber and water-absorptive contact lenses made predominantly of poly-2-hydroxyethyl methacrylate or polyvinyl pyrrolidone.

When these contact lenses are worn on eyes, secretions in the eyes, such as proteins or sebum, tend to deposit on the surfaces of the lenses. Therefore, upon removal from the eyes, the contact lenses must be cleaned to remove the deposited proteins or sebum from the lens surfaces. If inadequately cleaned contact lenses are inserted into eyes, they are likely to cause uncomfortable symptons such as foggy sight, pain or ocular injection, and in an extreme case, it will be necessary to stop wearing the contact lenses.

In a method commonly used for cleaning contact lenses, a cleaning solution comprising e.g. a higher alcohol ether is applied to both surfaces of the lenses and the lens surfaces are then rubbed with fingers. The cleaned contact lenses are rinsed with e.g. a physiological saline solution and then stored in a preservative solution comprising e.g. sodium chloride and a buffer.

Particularly in the case of water-absorptive contact lenses, the cleaning solution is likely to penetrate into the lenses during the cleaning operation because they are made of water absorptive material. Accordingly, it is likely that the cleaning solution remains absorbed in the lenses if the subsequent rinsing is inadequate, or some ingredients of the cleaning solution still remain in the lenses even after the rinsing. In view of the likeliness that such contact lenses as containing the cleaning solution will be inserted to eyes, it is necessary that the cleaning solution is made of ingredients which are harmless or safe to the ocular tissues.

Accordingly, the surface active agent to be used for the cleaning solution, should be selected from those having an adequate cleaning power and being harmless to the ocular tissues and stable.

In this respect, a block copolymer prepared by the addition of ethyleneoxide to both terminals of poly-propylene oxide, has been commonly used as the surface active agent. This block copolymer has desirable characteristics such that when used as a cleaning solution for water-absorptive contact lenses, it has little toxicity and is harmless or quite safe to the ocular tissues and by virtue of its great molecular weight, it is hardly penetrable into the contact lenses during the cleaning operation of the water-absorptive contact lenses.

However, when the ethyleneoxide content and the molecular weight of the block copolymer are adjusted to increase its cleaning power, the cloud point of the cleaning solution (i.e. the temperature at which the cleaning solution becomes turbit) tends to be low, or in some cases, the cloud point lowers as time passes due to the effect of light (i.e. ultraviolet ray), whereby the cleaning solution becomes turbid at a temperature of about 50 to about 70° C. Consequently, the cleaning power will be reduced, the stability will be lost and the above mentioned effectiveness can no longer be expected.

SUMMARY OF THE INVENTION

It is an object of the present invention to provide a cleaning composition for contact lenses, which is highly stable and harmless to the eyes and in which block copolymers prepared by the addition of ethyleneoxide to both terminals of poly-propylene oxide and being highly effective as a surface active agent, are used to provide an adequate cleaning power and the cloud point of the cleaning solution is raised by the block copolymers so that the turbidity is hardly formed.

The present invention provides a cleaning composition for contact lenses, which comprises, as the major component, one or both of polypropyleneoxide-polyethyleneoxide block copolymers (Pluronic type) and condensation products of polypropyleneoxide-polyethyleneoxide block copolymers with ethylene diamine (Tetronic type), in which said major component is a mixture of those having an ethyleneoxide content of from 35 to 55% by weight and a molecular weight of from 1,500 to 10,000 and those having an ethyleneoxide content of from 70 to 90% by weight and a molecular weight of at least 4,000.

DETAILED DESCRIPTION OF THE PREFERRED EMBODIMENTS

The major component of the cleaning composition for contact lenses according to the present invention comprises polypropyleneoxide-polyethyleneoxide block copolymers (Pluronic type) and/or condensation products of such block copolymers with ethylene diamine (Tetronic type).

The Pluronic type block copolymers are block copolymers prepared by the addition of ethyleneoxide to both terminals of polypropylene oxide and they are represented by the formula

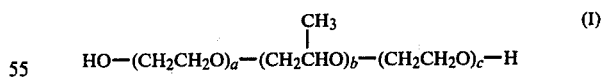

$$\text{HO}-(\text{CH}_2\text{CH}_2\text{O})_a-(\text{CH}_2\text{CHO})_b-(\text{CH}_2\text{CH}_2\text{O})_c-\text{H} \quad (\text{I})$$
$$\overset{|}{\text{CH}_3}$$

The block copolymers having an ethyleneoxide content of from 35 to 55% by weight and a molecular weight of from 1,500 to 10,000 are represented by the above formula (I) where $a+c$ is from 11.9 to 125.0 and b is from 11.6 to 112.1. Whereas the block copolymers having an ethyleneoxide content of from 70 to 90% by weight and a molecular weight of at least 4,000 are represented by the above formula (I) where $a+c$ is at least 63.6 and b is at least 6.9.

The Tetronic type condensation products are represented by the formula

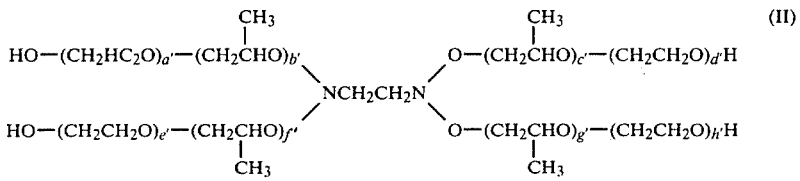

The condensation products having an ethyleneoxide content of from 35 to 55% by weight and a molecular weight of from 1,500 to 10,000 are represented by the above formula (II) where $a'+d'+e'+h'$ is from 11.9 to 125.0 and $b'+c'+f'+g'$ is from 11.6 to 112.1. Whereas the condensation product having an ethyleneoxide content of from 70 to 90% by weight and a molecular weight of at least 4,000 are represented by the above formula (II) where $a'+d'+e'+h'$ is at least 63.6 and $b'+c'+f'+g'$ is at least 6.9.

The block copolymers or the condensation products exhibit the maximum cleaning power when their ethyleneoxide content is from 35 to 55% by weight. The molecular weight of the block polymers or the condensation product is preferably from 1,500 to 10,000. If the molecular weight is less than 1,400, the cleaning power is remarkably reduced. The upper limit of the molecular weight is not critical. However, as the molecular weight becomes greater, the greater amount (i.e. the higher concentration) of the block copolymers and/or the condensation products is required to remove the same amount of contaminants. For these reasons, it is preferred that the block copolymers or the condensation products have an ethyleneoxide content of from 35 to 55% by weight and a molecular weight of from 1,500 to 10,000, especially from 1,500 to 6,000.

When these block copolymers and/or the condensation products are used as a component of a cleaning solution for contact lenses, they exhibit excellent cleaning effectiveness. However, as mentioned above, their cloud point is relatively low and tends to lower as time passes due to the effect of light (i.e. ultraviolet ray) or high temperature, and it is likely that turbidity will form and the stability becomes poor, thus leading to practical disadvantages.

Whereas, when the above block copolymers and/or the condensation products are used in combination with analogous block copolymers and/or the condensation products having an ethyleneoxide content of from 70 to 90% by weight and a molecular weight of at least 4,000, the cloud point becomes higher and the stability against light (i.e. ultraviolet ray) and temperature is improved, whereby turbidity is hardly formed. Thus, a satisfactory condition for practical applications can thereby be obtained. In this case, it is further observed that the cleaning power is improved by the combined use of the block copolymers and/or the condensation products since the combined block copolymers and/or the condensation products have a greater ability to disperse the contaminants.

If the molecular weight of the block copolymers or the condensation products to be combined, is less than 4,000, such block copolymers or the condensation products do not very much contribute to the improvement of the cleaning power since the ability to disperse contaminants is thereby poor. The upper limit of the molecular weight is not critical. However, if the molecular weight becomes too great, the molecular structures of the block copolymers or the condensation products become unstable. For the stability of the molecular structures, the upper limit of the molecular weight is about 50,000.

The weight ratio of the block copolymers and/or the condensation products having an ethyleneoxide content of from 35 to 55% by weight and a molecular weight of from 1,5000 to 10,000 to the block copolymers and/or the condensation products having an ethyleneoxide content of from 70 to 90% by weight and a molecular weight of at least 4,000, is preferably from 10:1 to 1:30, more preferably from 2:1 to 1:10.

In the case of an aqueous solution, it is preferred that the cleaning solution contains from 0.05 to 5% by weight of the block copolymers and/or the condensation products having an ethyleneoxide content of from 35 to 55% by weight and a molecular weight of from 1,500 to 10,000 and from 0.05 to 10% by weight of the block copolymers and/or the condensation products having an ethyleneoxide content of from 70 to 90% by weight and a molecular weight of at least 4,000. The total amount of the two kinds of the block copolymers and/or the condensation products is preferably from about 0.1 to about 15% by weight in the cleaning solution.

In the preparation of the cleaning composition for contact lenses according to the present invention, the surface active agent composed of the above mentioned mixture of the block copolymers and/or the condensation products is used as the essential ingredient. As an auxiliary ingredient, it is preferred to use a buffer to stabilize the pH of the solution. As the buffer, there may be mentioned a physiologically acceptable buffer such as sodium hydrogencarbonate, boric acid and its sodium salt, phosphoric acid and its sodium salt, citric acid and its sodium salt, lactic acid and its sodium salt, malic acid and its sodium salt. Such a buffer is used in a concentration of from about 0.01 to about 1 mol/liter, preferably from about 0.15 to about 0.03 mol/liter. When the cleaning composition for contact lenses of the present invention is used in a form of an aqueous solution, the buffer serves to stabilize the aqueous solution, maintain the aqueous solution at a pH of from 6.0 to 8.0, preferably from 7 to 7.4 which is substantially equal to the pH of the tear fluid in eyes, and stabilize the standardized configuration of the contact lenses.

Further, a viscosity builder may be added to the cleaning composition of the present invention to give a proper viscosity to the solution so that the cleaning operation can thereby be facilitated. As such a viscosity building agent, there may be mentioned, for instance, polyvinyl alcohol, polyethylene glycol, methyl cellulose, carboxymethyl cellulose or dextrane, and it is preferably added in an amount of from about 0.1 to about 5% by weight in the solution.

In order to impart the bactericidal and antiseptic properties to the cleaning composition of the present invention, a proper physiologically acceptable germicide may be incorporated. As the germicide which may be used in the present invention, there may be mentioned thimerosal, chlorohexidine, phenylmercuric nitrate, benzalkonium chloride, chlorobutanol, bronopol or sodium benzoate. The amount of the germicide to be incorporated varies depending upon the kind of the germicide, but it is usually from 0.0001 to 1.0% by weight in the solution.

Further, if necessary, from about 0.1 to about 0.9% by weight of a tonicity agent such as sodium chloride to bring the osmotic pressure of the cleaning solution equivalent to that of tear fluid in eyes, a chelating agent such as ethylenediamine tetraacetate to prevent deposition of e.g. a calcium salt, a hydrogen bond destroying agent such as urea or guanidine or a salt such as sodium thiocyanate which provides a salting-in effect, may further be added to the cleaning composition of the present invention. It is also possible to use other surface active agents in combination with the surface active agent of the present invention.

The contact lens cleaning composition of the present invention may be formulated in a form of an aqueous solution or in a form of granules.

In the case of the aqueous solution, a predetermined amount of purified water is used as the solvent, and the above mentioned various ingredients are added thereto and sufficiently stirred to obtain a solution. After adjusting the pH, the solution is filtered to obtain the desired cleaning solution.

In the preparation of a granular product, the above mentioned ingredients are pulverized and mixed and stirred in a predetermined amount of purified water. If necessary, a vehicle is added thereto and the mixture is kneaded. After passing through a mesh, the mixture is heated under reduced pressure for drying to form granules.

In actual use, the granules are dissolved in a predetermined amount of purified water or distilled water to obtain an aqueous solution, and the contact lenses are cleaned with the aqueous solution.

Now, the present invention will be described in detail with reference to the Examples. In the Examples, polypropyleneoxide-polyethyleneoxide block copolymers (Pluronic type) are referred to as "P-component", and condensation products of the polypropyleneoxide-polyethyleneoxide block copolymers with ethylenediamine (Tetronic type) are referred to as "T-component".

EXAMPLE 1

| P-component: | |
|---|---|
| Ethyleneoxide content: 40% by weight | 0.5 |
| Molecular weight: 3,333 | |
| P-component: | |
| Ethyleneoxide content: 80% by weight | 0.5 |
| Molecular weight: 10,000 | |
| Sodium chorlide | 0.9 |
| Polyethylene glycol | 3.0 |

The above ingredients (the numerical values represent % by weight in 100 cc of an aqueous solution, the same applies hereinafter) were put in purified water, thoroughly mixed and stirred, and dissolved to form an aqueous solution. The aqueous solution was adjusted to pH 7.4 with sodium hydrogencarbonate to obtain a cleaning composition (liquid).

EXAMPLE 2

| P-component: | |
|---|---|
| Ethyleneoxide content: 40% by weight | 0.35 |
| Molecular weight: 3,333 | |
| P-component: | |
| Ethyleneoxide content: 80% by weight | 0.7 |
| Molecular weight: 10,000 | |
| Sodium chloride | 0.9 |
| Polyvinyl alcohol | 1.7 |

In the same manner as in Example 1, a cleaning composition (liquid) containing the above ingredients was obtained.

EXAMPLE 3

| P-component: | |
|---|---|
| Ethyleneoxide content: 35% by weight | 0.3 |
| Molecular weight: 5,000 | |
| P-component: | |
| Ethyleneoxide content: 80% by weight | 1.0 |
| Molecular weight: 8,500 | |
| Sodium chloride | 0.9 |
| Polyethylene glycol | 3.0 |

In the same manner as in Example 1, a cleaning composition (liquid) containing the above ingredients was obtained.

EXAMPLE 4

| T-component: | |
|---|---|
| Ethyleneoxide content: 40% by weight | 0.35 |
| Molecular weight: 5,000 | |
| T-component: | |
| Ethyleneoxide content: 70% by weight | 1.05 |
| Molecular weight: 12,000 | |
| Sodium chloride | 0.9 |
| Methyl cellulose | 0.5 |

In the same manner as in Example 1, a cleaning composition (liquid) containing the above ingredients was obtained.

EXAMPLE 5

| T-component: | |
|---|---|
| Ethyeneoxide content: 40% by weight | 0.5 |
| Molecular weight: 5,000 | |
| P-component: | |
| Ethyleneoxide content: 80% by weight | 0.5 |
| Molecular weight: 10,000 | |
| Sodium chloride | 0.9 |
| Methyl cellulose | 0.7 |

In the same manner as in Example 1, a cleaning composition (liquid) containing the above ingredients was obtained.

EXAMPLE 6

| P-component: | |
|---|---|
| Ethyleneoxide content: 40% by weight | 0.5 |
| Molecular weight: 3,333 | |
| T-component: | |
| Ethyleneoxide content: 80% by weight | 1.0 |
| Molecular weight: 26,600 | |
| Sodium chloride | 0.9 |

-continued

| | |
|---|---|
| Polyvinyl alcohol | 2.0 |

In the same manner as in Example 1, a cleaning composition (liquid) containing the above ingredients was obtained.

EXAMPLE 7

| | |
|---|---|
| P-component: | |
| Ethyleneoxide content: 40% by weight | 0.35 |
| Molecular weight: 3,333 | |
| P-component: | |
| Ethyleneoxide content: 80% by weight | 0.7 |
| Molecular weight: 10,000 | |
| Citric acid | 1.31 |
| Sodium chloride | 0.25 |
| Disodium ethylenediaminetetraacetate | 0.10 |
| Polyethylene glycol | 3.0 |
| Thimerosa | 0.004 |

The above ingredients were dissolved in the same manner as in Example 1 to obtain an aqueous solution. The aqueous solution was adjusted to pH 7.4 with sodium hydroxide to obtain a cleaning composition (liquid).

EXAMPLE 8

| | |
|---|---|
| P-component: | |
| Ethyleneoxide content: 35% by weight | 0.4 |
| Molecular weight: 5,000 | |
| P-component: | |
| Ethyleneoxide content: 80% by weight | 1.0 |
| Molecular weight: 8,500 | |
| Malic acid | 0.91 |
| Sodium chloride | 0.25 |
| Disodium ethylenediaminetetraacetate | 0.10 |
| Methyl cellulose | 0.5 |
| Sodium benzoate | 0.5 |

In the same manner as in Example 7, a cleaning composition (liquid) containing the above ingredients was obtained.

EXAMPLE 9

| | |
|---|---|
| T-component: | |
| Ethyleneoxide content: 40% by weight | 0.5 |
| Molecular weight: 5,000 | |
| P-component: | |
| Ethyleneoxide content: 80% by weight | 1.0 |
| Molecular weight: 10,000 | |
| Citric acid | 1.31 |
| Sodium chloride | 0.25 |
| Disodium ethylenediaminetetraacetate | 0.10 |
| Polyethylene glycol | 3.0 |
| Thimerosal | 0.004 |

In the same manner as in Example 7, a cleaning composition (liquid) containing the above ingredients was obtained.

Now, the test results of the contact lens cleaning compositions obtained by the Examples will be described.

Comparative test for the cloud point:

A cleaning composition (liquid) was prepared in the same manner as in Example 1 except that as the surface active agent, the P-component having an ethyleneoxide content of 40% by weight and a molecular weight of 3,333 as used in Example 1 and having a very strong cleaning power was used alone. The cloud point of this cleaning composition was about 54° C.

Whereas, the cloud point of the cleaning composition obtained by Example 1 was about 82° C. Thus, the cloud point was improved by about 28° C.

Stability test:

One hundred ml of each of the cleaning compositions obtained by Examples 1 to 9 was put in a contact lens solution container (Tradename: $O_2$-Care Bottle manufactured by Toyo Contact Lens Co., Ltd.) One such sample was left to stand outdoors and another such sample was left at a temperature of 70° C.

At predetermined intervals (i.e. one month later, 2 months later and 3 months later), each aqueous solution was examined. No turbidity was observed in any one of them, and it was found that each composition was a stable aqueous solution.

Safety test:

Into one eye of each of 9 white rabbits, 0.1 ml of each cleaning composition obtained by Examples 1 to 9 was dropped, and the other untreated eye was used as the control. After 30 minutes from the dropping, the frontal ocular tissue was inspected. The frontal ocular tissue inspection was performed by observing with naked eyes conjunctival hyperemia, iris injection, sebum and corneal clouding, and by observing the corneal epithelium desquamation by a slit lamp.

No abnormality was observed in the treated eye as well as in the untreated eye of any one of the tested rabbits. Thus, no problem was indicated with respect of the safety to eyes.

Test for the cleaning power:

Commercially available fresh water-absorptive contact lenses (Tradename: Menicon Soft A, manufactured by Toyo Contact Lens Co., Ltd.) were placed in 54 eyes of 27 patients (i.e. users of water-absorptive contact lenses). The 27 patients were divided into 9 groups each consisting of 3 patients (6 eyes). The 9 groups of the patients were assigned to use the cleaning compositions obtained by Examples 1 to 9, respectively, in a usual manner (i.e. when removed from the eyes, the contact lenses were cleaned by applying a sufficient amount of the cleaning composition to the lenses and rubbing them with finger tips).

At predetermined intervals (i.e. 1 month later, 2 months later and 3 months later), the surface of each lens was inspected. The inspection was performed by means of a projector and a slit lamp in comparison with a fresh water-absorptive contact lens of the above mentioned type.

As the results, it was found that all the lenses applied to 54 eyes of the 27 patients and cleaned with the cleaning compositions obtained by Examples 1 to 9 showed the surface states substantially the same as the fresh contact lens. Thus, it was confirmed that all of the cleaning compositions had adequate cleaning effects.

As is apparent from the foregoing, the cleaning compositions for contact lenses of the present invention are superior in their cleaning power and safety and have a high cloud point and stability, whereby they remain stable for a long period of time without forming turbidity.

We claim:

1. A cleaning composition for contact lenses, which comprises, as the major component a mixture of (A) at least one member selected from the group consisting of (a), polypropyleneoxide-polyethyleneoxide block copolymers having an ethyleneoxide content of from 33 to 55% by weight and a molecular weight of from 1,500 to 10,000 and (b) condensation products of polypropyleneoxide-polyethyleneoxide block copolymers with ethylene diamine having an ethyleneoxide content of from 35 to 55% by weight and a molecular weight of from 1,500 to 10,000 and (B) at least one member selected from the group consisting of (a$_1$) polypropyleneoxide-polyethyleneoxide block copolymers having an ethyleneoxide content of from 70 to 90% by weight and a molecular weight of at least 4,000 and (b$_1$) condensation products of polypropyleneoxide-polyethyleneoxide block copolymers with ethylene diamine having an ethyleneoxide content of from 70 to 90% by weight and a molecular weight of at least 4000, wherein the weight ratio of (A):(B) is from 10:1 to 1:30.

2. The cleaning composition according to claim 1 wherein the block copolymers are represented by the formula

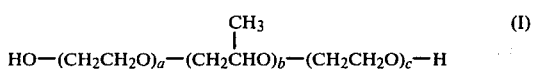

and the condensation products are represented by the formula

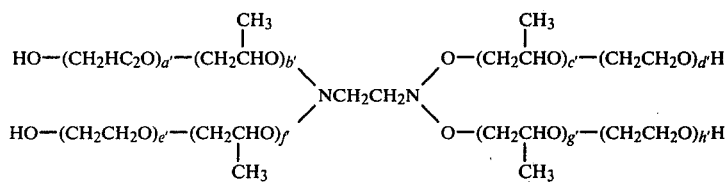

and said major component is a mixture of (A) at least one member selected from (a) the block copolymers represented by the above formula (I) where a+c is from 11.9 to 125.0 and b is from 11.6 to 112.1 and (b) the condensation products represented by the above formula (II) were a'+d'+e'+h' is from 11.9 to 125.0 and b'+c'+f'+g' is from 11.6 to 112.1 and (B) at least one member selected from (a$_1$) the block copolymers represented by the above formula (I) where a+c is at least 63.6 and b is at least 6.9 and (b$_1$) the condensation products represented by the above formula (II) where a'+d'+e'+h' is at least 63.6 and b'+c'+f'+g' is at least 6.9.

3. The cleaning composition according to claim 1 wherein at least one member is selected from (a$_1$) the block copolymers and (b$_1$) the condensation products having an ethyleneoxide content of from 70 to 90%, have a molecular weight of from 4,000 to 50,000.

4. The cleaning composition according to claim 1 which is in a form of an aqueous solution containing from 0.05 to 5% by weight of (A) at least one member selected from (a) the block copolymers having an ethylene oxide content of from 35 to 55% by weight and a molecular weight of from 1500 to 10,000 and (b) the condensation products having an ethyleneoxide content of from 35 to 55% by weight and a molecular weight of from 1,500 to 10,000 and from 0.05 to 10% by weight of (B) at least one member selected from (a$_1$) the block copolymers having an ethyleneoxide content of from 70 to 90% by weight and a molecular weight of at least 4,000 and (b$_1$) the condensation products having an ethyleneoxide content of from 70 to 90% by weight and a molecular weight of at least 4,000.

5. The cleaning composition according to claim 4 wherein the solution contains from about 0.01 to about 1 mole/liter of a physiologically acceptable buffer to maintain the solution at a pH of from 6.0 to 8.0.

6. The cleaning composition according to claim 5 wherein the buffer is selected from sodium hydrogencarbonate, boric acid and its sodium salt, phosphoric acid and its sodium salt, citric acid and its sodium salt, lactic acid and its sodium salt, malic acid and its sodium salt.

7. The cleaning composition according to claim 4 wherein the solution contains from about 0.1 to about 5% by weight of a physiologically acceptable viscosity builder.

8. The cleaning composition according to claim 7 wherein the viscosity building agent is selected from polyvinyl alcohol, polyethylene glycol, methyl cellulose, carboxymethyl cellulose and dextrane.

9. The cleaning composition according to claim 4 wherein the solution contains from 0.0001 to 1.0% of a physiologically acceptable germicide.

10. The cleaning composition according to claim 9 wherein the germicide is selected from thimerosal, chlorohexidine, phenylmercuric nitrate, benzalkonium chloride, chlorobutanol, bronopol and sodium benzoate.

11. The cleaning composition according to claim 4 wherein the solution contains a tonicity agent in an amount of from about 0.1 to about 0.9% by weight to bring the osmotic pressure of the solution to that of tear fluid in eyes.

12. The cleaning composition according to claim 11 wherein the tonicity agent is sodium chloride.

13. The cleaning composition according to claim 4 wherein the solution contains a chelating agent, a hydrogen bond destroying agent, or a salt having a salting-in effect.

* * * * *